(12) United States Patent
Rustomjee

(10) Patent No.: US 11,638,691 B2
(45) Date of Patent: May 2, 2023

(54) ANTI CHAFING GEL COMPOSITION

(71) Applicant: AMATERASU LIFESCIENCES LLP, Mumbai (IN)

(72) Inventor: Maharukh Rustomjee, Mumbai (IN)

(73) Assignee: AMATERASU LIFESCIENCES LLP, Mumbai (IN)

( * ) Notice: Subject to any disclaimer, the term of this patent is extended or adjusted under 35 U.S.C. 154(b) by 0 days.

(21) Appl. No.: 16/630,864

(22) PCT Filed: Jul. 17, 2018

(86) PCT No.: PCT/IN2018/050463
§ 371 (c)(1),
(2) Date: Jan. 14, 2020

(87) PCT Pub. No.: WO2019/016830
PCT Pub. Date: Jan. 24, 2019

(65) Prior Publication Data
US 2020/0146985 A1 May 14, 2020

(30) Foreign Application Priority Data
Jul. 18, 2017 (IN) .............................. 201721025474

(51) Int. Cl.
| | | |
|---|---|---|
| *A61K 9/06* | (2006.01) | |
| *A61K 31/12* | (2006.01) | |
| *A61K 36/185* | (2006.01) | |
| *A61K 36/28* | (2006.01) | |
| *A61K 36/30* | (2006.01) | |
| *A61K 36/53* | (2006.01) | |
| *A61K 36/58* | (2006.01) | |
| *A61K 36/61* | (2006.01) | |
| *A61K 36/63* | (2006.01) | |
| *A61K 36/77* | (2006.01) | |
| *A61K 36/889* | (2006.01) | |
| *A61K 47/34* | (2017.01) | |

(52) U.S. Cl.
CPC ................ *A61K 9/06* (2013.01); *A61K 31/12* (2013.01); *A61K 36/185* (2013.01); *A61K 36/28* (2013.01); *A61K 36/30* (2013.01); *A61K 36/53* (2013.01); *A61K 36/58* (2013.01); *A61K 36/61* (2013.01); *A61K 36/63* (2013.01); *A61K 36/77* (2013.01); *A61K 36/889* (2013.01); *A61K 47/34* (2013.01)

(58) Field of Classification Search
None
See application file for complete search history.

(56) References Cited

FOREIGN PATENT DOCUMENTS

| | | |
|---|---|---|
| EP | 3072915 A1 | 9/2016 |
| EP | 3143984 A1 | 3/2017 |
| WO | 2016052571 A1 | 4/2016 |
| WO | 2017003139 A1 | 1/2017 |
| WO | 2018143061 A1 | 8/2018 |

OTHER PUBLICATIONS

International Search Report issued in PCT/IN2018/050463, dated Nov. 16, 2018, pp. 1-4.

*Primary Examiner* — Michael V Meller
(74) *Attorney, Agent, or Firm* — ArentFox Schiff LLP

(57) ABSTRACT

A gel composition comprising silicone crosspolymer and silicone oil wherein the composition when applied to the skin adheres to the skin with a work of adhesion of more than about 0.500 Newton·sec when measured by TA.XT plus text analyzer using a mucoadhesive rig and forms a film with a coefficient of friction of less than 0.400 when measured by Automatic surface tester (method ASTM D 1894).

10 Claims, 1 Drawing Sheet

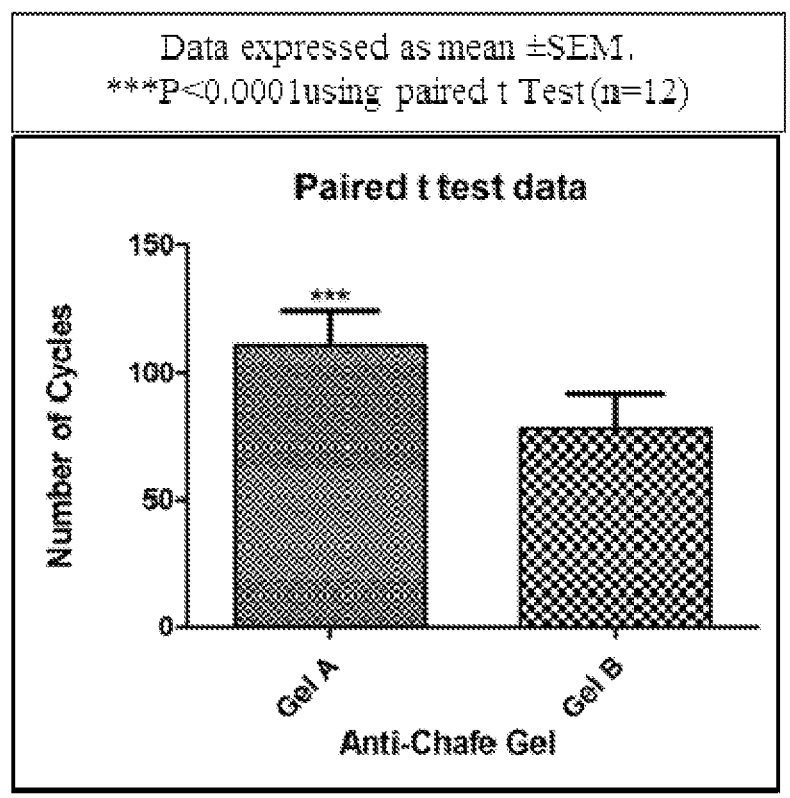
Two tailed 'Paired t Test' of clinical trials in Example 3

ANTI CHAFING GEL COMPOSITION

RELATED ART

United States patent publication no. 20060159645 (referred to herein as '645 application; Applicant M/s JOHNSON & JOHNSON) discloses silicone topical compositions for the prevention and/or treatment of chafing. The composition post application to the skin dries to a powder-like consistency. The '645 application does not suggest adhesive and abrasive resistant properties of the composition. The gel composition of the present invention forms a barrier film which lowers the friction on the skin surface post application. Further, it results in a smooth, non-powdery feel with good adhesive and abrasive resistant properties. Further, the composition of the present invention also has a long lasting effect.

U.S. Pat. No. 8,663,665 (referred to herein as '665 patent; assigned to M/S Momentive Performance Materials Inc.) teaches an anti-chafing composition comprising an effective amount of boron nitride. The gel composition of the present invention is devoid of boron nitride but still forms a film with low friction which has long lasting effect.

U.S. Pat. No. 9,393,261 (referred to herein as '261 patent; assigned to M/s Body Glide LLC) discloses an anti-chafing balm comprising chelated silver oxide. The gel composition of the present invention is devoid of the expensive silver oxide.

U.S. Pat. No. 8,778,406 (referred to herein as '406 patent; assigned to M/s Joyce Labs, LLC) teaches an aerosol composition with zinc oxide which prevents or mitigates irritation on the skin by protecting against or relieving chafing and itching. The gel composition of the present invention is not an aerosol composition and does not contain zinc oxide.

U.S. Pat. No. 6,949,249 (referred to herein as '249; assigned to M/s JOHNSON & JOHNSON) teaches a spray pumpable liquid composition which has suitable adherence to the skin. The gel composition of the present invention is a gel.

PCT publication WO2017213505 (referred to herein as '505) teaches antichafing spray compositions devoid of silicone elastomer crospolymers. The gel composition of the present invention is a gel comprising silicone elastomer crospolymers.

U.S. Pat. No. 9,511,034 (referred to herein as '034; assigned to M/S Biosilicote Inc.) teaches a method of treating burns, wounds, scars and keloids. The composition of the present invention prevents chafing and treats the abrasion of the skin surface caused by chafing by application of a single gel composition comprising silicone crosspolymers.

The present invention relates to gel composition and its use to prevent or treat chaf, razor burns, itching and/or scar rash on a skin surface. The gel composition of the present invention when applied on the skin surface demonstrates excellent anti friction properties and abrasion resistance. The gel of the present invention imparts lubrication to skin surfaces, protects the skin surfaces from irritation, inflammation, chafing and may assist in preventing injury to the skin surfaces, thus avoiding violation or infection of the surfaces.

BACKGROUND OF THE INVENTION

Skin when exposed to constant friction may become irritated, chaffed and could get injured. This can be a particular problem among many human, whether caused by constant rubbing against another skin surface or by frictional exposure to an external surface such as cloth or solid surfaces depending upon the human's activity.

Chafing occurs where parts of the skin such as on the inner thighs, groin areas, armpits, nipples, etc. as a consequence of resistance from body parts rubbing jointly, or resistance from clothing and sweating. Chafing also occurs on the feet due to rubbing and friction with parts of footwear especially if it is new. Chafing mostly occurs around the bra line (in the women), nipples (in the men), inner thighs, groin areas, and under arms. Chafing gets aggravated while undergoing physical activities such as walking, running, swimming, playing sports and other movement oriented activities. Hot and humid climatic conditions and bad lifestyle practices such as wearing synthetic or tight fitting clothes/footwear, overcrowding and excessive travel in congested areas further increases risk for chafing. It is also aggravated due to excess body weight in overweight and obese people, diabetics, people suffering from thyroid and genitourinary disorders and immune compromised people. Causes of chafing are frequent motion—particularly, skin resistance against movable fabric or other skin.

Common symptoms of chafing is painful stinging or burning feeling. Chafing is associated with rash, redness, tearing or scraping of the skin exposing the skin to possible infection. Use of products to soothe skin and alleviate chafing is well known, and there have been a variety of products available on the market to perform the required function such as powders, petroleum jelly, ointments, oils, lotions, creams and the like. Some of them such as ointments, lotions spread to the clothing and stain it and may later lose their adherence to the skin. Particulate products may not provide to the human protection from chafing due to lower adherence to the skin and results in need for frequent application.

Hence, there is a need for a skin protectant which can cover the surface and forms a film which acts as a protective barrier and reduces the impact of friction to prevent and treat erythema and frictional dermatitis. However, most of the current remedies for chafing need to be applied frequently every couple of hours to maintain and give relief from the pain and irritation on the skin. This can be very inconvenient for patient as they need to frequently go to the rest rooms and apply the topical product, hence there is a need for a product with improved adherence and abrasion resistance resulting in a longer duration of protection.

Chafing is aggravated by sweating and as sweat creates a breeding area for germs such as bacteria and fungus it causes irritation and skin diseases. Further, the germs could enter the body via skin opening due to chafing. In order to avoid this phenomena the anti chafing composition of the present invention may comprise antimicrobial and/or anti-inflammatory agents.

The present invention relates to a gel composition which acts as a skin protectant and prevents or treats symptoms associated with chafing.

OBJECT OF THE INVENTION

The object of the present invention is to provide a gel composition which provides a film with beneficial properties such as low coefficient of friction and adheres to the skin. Further, the film has high abrasion resistance resulting in longer duration of protection for the skin against irritation/injury due to friction.

Another object of the present invention is to provide a gel product as described above which can be applied to the affected area to keep the skin dry and prevent conditions such as Athlete's foot (*Tinea pedis*), Jock Itch (*Tinea cruris*), Ringworm (*Tinea corporis*), Candidiasis and also prevent diaper rash and chafing commonly occurring in infants and geriatrics who are wearing diapers for long hours per day.

SUMMARY OF THE INVENTION

A gel composition comprising
(a) one or more silicone crosspolymer in about 1 to about 50% w/w of the composition and silicone oil in about 50 to about 99% w/w of the composition;
(b) sweat and/or sebum absorbing agent in about 0.1 to about 25% w/w of the composition;
(c) optionally non-volatile film forming polymer in about 0.1 to about 25% w/w of the composition;
(d) optionally skin rejuvenating and/or soothing agent in about 0.1 to about 25% w/w of the composition;
wherein the composition when applied to the skin adheres to the skin with a work of adhesion of more than about 0.500 Newton·sec when measured by TA.XT plus text analyzer using a mucoadhesive rig and forms a film with a coefficient of friction of less than 0.400 when measured by Automatic surface tester (ASTM D 1894).

BRIEF DESCRIPTION OF DRAWINGS

FIG. 1 illustrates the results of a Two tailed 'Paired t Test' of Abrasion Resistance Study on human panel in Example 5, wherein Gel A is the test product (composition of Example 3g) and Gel B is the marketed product (Refle sport).

DESCRIPTION OF THE INVENTION

Chafing is a friction-induced injury to the skin, ranging from minor irritation or abrasion where layers of the skin are worn away, or ruptured. Moisture, salts and minerals excreted as perspiration often aggravate, accelerate and exasperate chafing. The effects of chafing are seen, for example, as rash, redness, burning sensation and discomfort during movement. Chafing includes conditions of skin irritation and inflammation namely erythema and frictional dermatitis, leading to a feeling of burning and discomfort on movement. Use of compounds to soothe skin and alleviate chafing is well known, and there have been a variety of products available on the market to perform the required function.

Chafing is a simple problem with potentially large impact and chances of infection. It is commonly seen in intimate areas. Majority of fungal and yeast infections such as *Tinea cruris* (jock itch), *Tinea corporis* (ringworm) and candidiasis begin with chafing. Doctors strongly feel the need for an early intervention to prevent chafing.

We have surprisingly found a gel composition which on application to the skin imparts dual properties of providing adhesion with a low coefficient of friction. The composition of the present invention has improved abrasion resistance leading to a long lasting action. It also provides a smooth and slippery feel.

According to one embodiment of the present invention is a gel composition comprising silicone crosspolymers and silicone oil wherein the composition when applied onto the skin in an effective amount adheres to the skin and forms an antifriction barrier film.

More specifically the gel composition of the present invention is an anti chafing gel composition.

The compositions useful in the methods of this invention relate to non-aqueous or anhydrous compositions. The composition of the present invention is preservative, colourant and fragrance free resulting in a hypoallergenic composition.

The gel composition of the present invention adheres to the skin and with a work of adhesion of more than 0.500 Newton·sec when measured by TA.XTplus Texture analyzer using a mucoadhesive rig. Preferably, the work of adhesion is more than 0.600 Newton·sec when measured by TA.XTplus Texture analyzer using a mucoadhesive rig. The higher the adhesiveness the better the ability of the composition to adhere to the skin surface to form a protective film.

The gel composition of the present invention exhibits a coefficient of friction below 0.400 when measured by Automatic surface tester (method ASTM D 1894). Preferably, the coefficient of friction is below 0.300 when measured by Automatic surface tester (method ASTM D 1894). A lower coefficient of friction reflects improved anti-friction property of the composition. Lowering of friction on the skin surface helps to reduce the friction which is the cause of chafing, reduces irritation and chafing.

Additionally, the gel composition of the present invention spreads well and provides a smooth and slippery feel as compared to the prior known powdery feel.

We have surprisingly found that marketed products have good adhesion properties and coefficient of friction but unfortunately they do not protect the skin for longer duration as they have poor abrasion resistance.

The gel composition of the present invention when applied onto a substrate in an effective amount also imparts abrasion resistance of at least 10 cycles when measured by abrasion test IS12673-1989 or ASTM D 3885. Preferably, abrasion resistance of at least 12 cycles when measured by abrasion test IS12673-1989 or ASTM D 3885. The higher the number of cycles the better the abrasion resistance and the gel is retained on the skin for a longer time.

Further, the composition of the present invention when applied to the skin surface in an effective amount exhibits a significantly higher ability to be retained on the skin when exposed to forced abrasion using a dry sponge massager and thus providing a longer duration of protection.

The gel composition of the present invention comprises silicone crosspolymers in about 1 to about 50% w/w of the composition. Preferably, silicone crosspolymers in about 1 to about 30% w/w of the composition.

The silicone crosspolymer(s) may have an average molecular weight in excess of 10,000 (e.g., between about 10,000 and 10,000,000). Examples of silicone crosspolymers included but not limited to dimethicone/vinyldimethicone crosspolymers, dimethicone crosspolymers, dimethicone/phenyl vinyldimethicone crosspolymers, vinyldimethicone/methicone sil sesquioxane crosspolymers, dimethicone/PEG-10/15 crosspolymers, PEG-15/Lauryldimethicone crosspolymers and mixtures thereof.

The gel composition of the present invention comprises silicone oils in about 50 to about 99% w/w of the composition; included but not limited to dimethicone, cyclopentasiloxane, simethicone, methyl dimethicone, methyl trimethicone, phenyl siloxyphenyltrimethicone, trisiloxane and the like. Preferably, silicone oils are in about 70 to about 99% w/w of the composition The gel composition may comprise silicone elastomer gels which are blends of silicone crosspolymers and silicone oils.

The gel composition of the present invention may also comprise additional excipients such as sweat absorption, sebum absorption, skin rejuvenating, soothing agents, non-volatile film forming polymer ranging from 0.1 to 25%.

The amount of excipients in the gel composition of the present invention may be varied within wide parameters, but should be in a sufficient amount for the composition when applied on the skin to act as an antifriction barrier film on the applied surface of the skin such that the gel suitably adheres to the skin, and in any event, the composition effectively inhibits or reduces irritation or chafing to the skin caused by rubbing, whether skin against skin or against another object including, but not limited to apparel and footwear.

The sweat and/or sebum absorbing excipient(s) used in the present invention may be selected from but not limited to silica silylate, magnesium alumina meta silicate, engineered particles of silica, silicic acids and any types of derivatives and modifications thereof. Suitable examples comprise polysilicic acids, silicic anhydride, fumed silica, hydrated silica, silica gel, silicate esters and/or silicate salts such as sodium silicate magnesium silicate, calcium silicate and all types of starch and starch derivates. The sweat and sebum absorbing excipient(s) may be used in the range 0.1 to 25% by weight of the composition.

Preferred range of sweat and/or sebum absorbing excipient(s) when it does not comprise of starch and/or starch derivatives is less than 1.0% by weight of the composition; more preferably about 0.1% to about 0.5% w/w of the composition. The preferred range of sweat and/or sebum absorbing excipient(s) when it comprises of starch and/or starch derivatives is about 0.1 to about 15% w/w of the composition.

The non-volatile film forming polymer used in the present invention may be a composition of trimethylsiloxysilicate and the like. The non-volatile film forming polymer may be used in the range of about 0.1 to about 25% w/w of the composition. Preferably, about 0.1 to about 10% w/w of the composition.

The skin rejuvenating and/or soothing agent used in the present invention may be selected from curcumin analogs, Balloon Vine extract, Echium Oil, Blackcurrant seed oil, sunflower oil concentrate, tea tree oil, tulsi, neem oil, coconut oil, olive oil and the like. The skin rejuvenating and/or soothing agent may be used in the range about 0.1 to about 25% w/w of the composition. Preferably, about 0.1 to about 10% w/w of the composition.

The process used for the preparation of the composition of the present invention entails a cold mixing process without any heat. The crospolymer gel(s) are mixed in a mixer and the excipients dispersed in cyclopentasiloxane and/or dimethicone are added to the crosspolymer gel(s) and mixed.

The gel compositions of the present invention may be packaged in a container that is well known by an artisan of ordinary skill, e.g., low density polyethylene tube or laminated aluminum tubes with a dispensing tip head.

According to yet another embodiment of the present invention is a method of preventing or treating symptoms associated with a topical skin disorder in a human patient, the method comprising contacting a skin surface in need of such symptomatic prevention or treatment with the gel composition in an amount and period of time effective to symptomatically prevent or treat the skin disorder or symptoms of the skin disorder.

The skin disorder may be irritation of skin, chafing, razor burn, itching or pruritis, scar rash, diaper rash, athlete's foot (*Tinea pedis*), jock itch (*Tinea cruris*), ringworm (*Tinea corporis*) and candidiasis by application of gel composition of the present invention.

The symptoms associated with the skin disorder may be itching, burning, discomfort, numbness and tingling.

The gel composition of the present invention is applied to the skin one to three times daily. When used in treating chafing of one skin surface against another surface, the composition may be applied until the chafing or irritation is alleviated or it can be used prophylactically on a chronic basis. More preferably, the composition useful in the methods of this invention is applied to two or more surfaces that may come into contact with each other. The skin surfaces which come into contact with each other are the chafing prone areas and by application of the gel of the present invention the probability of chafing is reduced.

The human may also, in accordance with the methods of this invention, apply such compositions to his or her skin which may come into frequent contact with external clothing or shoes, in order to protect such skin from chafing, irritation and or blistering.

Definition of terms As used herein, the term "anti-chafing composition" means any topically applied composition comprising ingredients capable of reducing, relieving, or minimizing chafing from friction of human skin, particularly friction induced injury to the skin ranging from minor irritation or abrasion, resulting from the rubbing of skin against skin, clothing, shoes, or other materials. Chafing includes conditions of skin irritation and inflammation namely erythema and frictional dermatitis As used herein, the term "Abrasion resistance" means a property which allows a material to resist wearing off due to repetitive rubbing. The composition is expected to be retained on the skin for a longer time when it has a higher resistance to abrasion.

As used herein the term "Adhesiveness or Adhesive" is the force that resists the separation of two bodies in contact. The composition is expected to adhere to the skin when it has a higher work of adhesion.

As used herein, the term "Coefficient of Friction" means a value that shows the relationship between the force of friction between two objects and the normal force between the objects. It is the ratio of the force of friction between an object and a surface to the frictional force resisting the motion of the object.

As used herein the term "applied on to the skin in an effective amount" means the anti chafing composition being applied in an amount sufficient to cover the affected area of the skin.

As used herein the term "silicone elastomer gel" means a silicon crosspolymer blended with silicone oils.

The following examples illustrate preferred embodiments in accordance with the present invention without limiting the scope of the invention.

EXAMPLES

Example 1

Compositions of the Invention

| Excipients | % w/w | | | | | | |
|---|---|---|---|---|---|---|---|
| | 1a | 1b | 1c | 1d | 1e | 1f | 1g |
| Dimethicone/VinylDimethicone Crosspolymer | 5.7 | 6.4 | 6.4 | 6.1 | 3.6 | — | — |
| Dimethicone crosspolymer | 1.4 | — | — | — | 4.5 | 8.7 | 6.9 |
| Cyclopentasiloxane | 81.1 | 90.5 | 90.4 | 89.2 | 75.9 | 75.3 | 77.1 |
| Dimethicone | 8.6 | — | — | — | 12.9 | 12.9 | 12.9 |
| Corn starch | 3.0 | 3.0 | 3.0 | 3.0 | 3.0 | 3.0 | 3.0 |
| Silica Silylate | 0.1 | 0.1 | 0.1 | 0.1 | 0.1 | 0.1 | 0.1 |
| Magnesium alumina metasilicate | 0.1 | | 0.1 | 0.1 | — | — | — |
| Trimethyl siloxy silicate | — | — | — | 1.5 | — | — | — |
| Total | 100 | 100 | 100 | 100 | 100 | 100 | 100 |

The above examples were prepared by a cold mixing process without using any heat. The crosspolymer gels were mixed in a mixer. Corn starch, silicates were dispersed in cyclopentasiloxane/dimethicone and added to the gel mass. Other excipients were added and mixed.

The examples of the above compositions were tested for adhesiveness, coefficient of friction and resistance to abrasion.

The examples were tested for their adhesiveness to confirm that the protective barrier film of the invention would adhere to the skin and ensure the required effect.

Adhesiveness test was carried out for the above mentioned compositions and the test parameters were as follows:

Instrument used: TA.XT.plus Texture analyzer.
Probe: Mucoadhesion rig
Test Mode: Tension Pre-Test Speed: 0.50 mm/sec.
Test Speed: 0.10 mm/sec
Post-Test Speed: 0.10 mm/sec
Applied Force: 5.0 g
Return Distance: 15.0 mm
Contact time: 60 sec
Procedure:

Apply 200 µl of the sample on the sampling slot, measure the adhesivesness using the above parameters. Sample of a similar marketed product (Reflesport—marketed by Reckitt Benkiser) was also tested for adhesiveness. Sodium CMC gels were also prepared and tested as positive control and cyclopentasiloxane was tested as a negative control.

| Test ID | Work of Adhesion (Adhesiveness) N · sec | Test ID | Work of Adhesion (Adhesiveness) N · sec |
|---|---|---|---|
| Positive Control | | Negative control | |
| Sodium CMC 3% gel | 0.460 | Cyclopentasiloxane | 0.090 |
| Sodium CMC 4% gel | 0.792 | | |
| Test products | | | |
| Example 1a | 0.707 | Reflesport | 0.825 |
| Example 1b | 0.827 | | |
| Example 1c | 0.734 | | |
| Example 1d | 0.593 | | |
| Example 1 e | 0.690 | | |
| Example 1f | 0.716 | | |
| Example 1g | 0.482 | | |

Sodium CMC gels are reported in literature to have good adhesive properties and so the adhesive values of 3% and 4% gels could be considered as those desirable in the invention. The adhesiveness value of marketed product Reflesport was found to be good.

The coefficient of friction of the above examples was tested to understand the ability of the composition to reduce the friction on the surface on the substrate when applied.

The coefficient of friction was tested on the following equipment using parameters as listed below Instrument Name: Automatic Surface Tester
Model/Product No.: KES FB4—AUTO-A
Make: KES KATO TECH CO. LTD. Japan.
Method: Kawabata method (ASTM D 1894)

The samples (1 gm) were applied on a substrate of 20×20 cms size substrate and dried. The coefficient of friction was measured in the standard mode using 200 gms as the force applied and a friction contactor size of 10×10 mm.

| S No | Example | Coefficient of friction (MIU) |
|---|---|---|
| 1 | Example 1a | 0.160 |
| 2 | Example 1c | 0.168 |
| 3 | Example 1f | 0.166 |
| 4 | Reflesport | 0.172 |

The above results confirm that the surface of the substrate after application of the compositions of the inventions demonstrate the ability to reduce the friction of the surface by more than 80% as all the values of the coefficient of friction are below 0.200 MIU.

The examples were also tested for resistance to accelerated abrasion to help understand the strength of the protective film to withstand rubbing off and give a longer duration of protection.

The abrasion resistance test was conducted using the following equipment and parameters Standard Test Method No. customized based on ASTM D 3885/IS 12673-1989

Type of Abradant used: Zero Emery Paper
Type of Abrasion: Unidirectional
Instrument Name: Universal Wear Tester
Model/Product No.: M282
Make: SDL ATLAS, HONG KONG
Air Pressure Used: 4 psi
Load Used: 0.5 lb
Mode: Unidirectional
Stroke Length: 1 inch The samples of the above example were mixed with a colourant and applied as a uniform layer on the substrate fabric. The films were dried and then subjected to abrasion on the equipment measured as number of cycles required to remove the coloured film.

The cycles required to peel off the film for the examples was as given below. A sample of the marketed product with a similar composition (Reflesport—marketed by Reckitt benkiser) was also tested for comparison

| S No | Example | Observation (No of cycle/s to peel off) |
|---|---|---|
| 1 | Example 1a | 50 |
| 2 | Example 1c | 15 |
| 4 | Reflesport | 05 |

1a and 1c showed very good adhesive values (above 0.700 N·sec) and abrasion resistance of more than 10 cycles.

Example 2

Compositions of the Invention

| Excipients | % w/w | | | | | | |
|---|---|---|---|---|---|---|---|
| | 2a | 2b | 2c | 2d | 2e | 2f | 2g |
| Dimethicone/Vinyl Dimethicone Cross polymer | 6.0 | 5.4 | 5.6 | 6.0 | 5.8 | 5.7 | 5.2 |
| Dimethicone crosspolymer | — | 2.1 | 1.4 | 0.7 | 0.7 | 0.7 | 2.1 |
| Cyclopentasiloxane | 89.0 | 76.5 | 81.2 | 85.8 | 85.2 | 84.6 | 76.6 |
| Dimethicone | — | 12.9 | 8.6 | 4.3 | 4.3 | 4.3 | 12.9 |
| Corn starch | 5.0 | 3.0 | 3.0 | 3.0 | 3.0 | 3.0 | 3.0 |
| Silica Silylate | — | 0.1 | 0.1 | 0.1 | 0.1 | 0.1 | 0.1 |
| Magnesium alumina metasilicate | — | — | 0.1 | 0.1 | 0.1 | 0.1 | 0.1 |
| Trimethyl siloxy silicate | — | — | — | — | 0.75 | 1.5 | — |
| Total | 100 | 100 | 100 | 100 | 100 | 100 | 100 |

The above examples were all prepared using the cold mixing process as explained in example 1.

The compositions were tested for adhesiveness, coefficient of friction and resistance to abrasion

| Example No | Work of Adhesion N · sec | Coefficient of Friction MIU | Resistance to abrasion in no of cyles to peel off |
|---|---|---|---|
| Example 2a | 0.809 | — | — |
| Example 2 b | 0.762 | — | — |
| Example 2 c | 0.696 | — | 60 |
| Example 2 d | 0.671 | 0.252 | 60 |
| Example 2 e | 0.646 | — | 45 |
| Example 2 f | 0.637 | — | 60 |
| Example 2 g | 0.701 | 0.222 | 30 |

The examples demonstrated good adhesiveness properties along with a low coefficient of friction. Further, many of them exhibit a significantly a very good resistance to abrasion as compared to the marketed sample. Thus, the inventive composition has a longer retention on the skin and expected to have a longer duration of anti friction action when applied to the skin.

Example 3

Compositions of the Invention

| Excipients | % w/w | | | | | | | |
|---|---|---|---|---|---|---|---|---|
| | 3a | 3b | 3c | 3d | 3e | 3f | 3g | 3h |
| Dimethicone/VinylDimethicone Cross polymer | 5.3 | 5.8 | 5.6 | 5.6 | 7.2 | 5.3 | 5.7 | 5.6 |
| Dimethicone crosspolymer | 0.8 | 0.7 | 0.7 | 0.7 | — | 0.8 | 1.4 | 0.7 |
| Cyclopentasiloxane | 83.5 | 83.5 | 81.4 | 81.4 | 85.9 | 78.5 | 81.0 | 81.9 |
| Dimethicone | 5.2 | 4.3 | 4.3 | 4.3 | 3.8 | 5.2 | 8.6 | 4.3 |
| Corn starch | 5.0 | 5.0 | 7.0 | 7.0 | 3.0 | 5.0 | 3.0 | 7.0 |
| Silica Silylate | 0.1 | 0.5 | 1.0 | — | 0.1 | 0.1 | 0.1 | 0.5 |
| Magnesium alumina metasilicate | 0.2 | 0.25 | — | 1.0 | 0.1 | 0.2 | 0.2 | — |
| Black currant seed oil, balloon vine extract, sunflower oil concentrate in Octyldodecanol | — | — | — | — | — | 5.0 | — | — |
| Total | 100 | 100 | 100 | 100 | 100 | 100 | 100 | 100 |

The above examples were all prepared using the cold mixing process as explained in example 1.

The compositions were tested for adhesiveness, coefficient of friction and resistance to abrasion

| Example No | Work of Adhesion N · sec | Coefficient of Friction MIU | Resistance to abrasion in no of cyles to peel off |
|---|---|---|---|
| Example 3 a | 0.646 | 0.272 | 14 |
| Example 3 b | 0.638 | — | — |
| Example 3 c | 0.186 | — | — |
| Example 3 d | 0.680 | — | — |
| Example 3 e | 0.732 | — | — |
| Example 3 f | 0.837 | — | — |
| Example 3 g | 0.695 | 0.260 | 13 |
| Example 3 h | 0.555 | — | — |

Example 4

Exemplary Compositions of the Invention

| Ingredient | Function | Optional/Required |
|---|---|---|
| Dimethicone/VinylDimethicone Cross polymer | Film forming agent, thickener and Gel forming agent | Required |
| Dimethicone crosspolymer | Film forming agent, thickener and Gel forming agent | Required |
| Phenyl vinyl Dimethicone crosspolymers | Film forming agent, thickener and Gel forming agent | Required |
| Vinyl dimethicone/ Methiconesilsesquioxane crosspolymer | Film forming agent, thickener and Gel forming agent | Required |
| Dimethicone/PEG-10/15 crosspolymer | Film forming agent, thickener and Gel forming agent | Required |
| PEG-15/lauryl dimethicone crosspolymer | Film forming agent, thickener and Gel forming agent | Required |
| Cyclopentasiloxane | Base Vehicle - Silicone oil/fluid | Required |
| Trisiloxane | Base Vehicle - Silicone Oil/fluid | |
| Methyl Trimethicone | Base Vehicle - Silicone oil/fluid | Required |
| Diphenyl siloxy phenyl Trimethicone and/or phenyl silicone oils | Base Vehicle - Silicone oil/fluid | Required |
| Dimethicone | Base Vehicle - Silicone oil/fluid | Required |
| Corn starch | Sebum and Sweat absorbent | Required |
| Silica Silylate | Sebum and Sweat absorbent | Required |
| Silicate Esters | Sebum and Sweat absorbent | Required |
| Silicate Salts | Sebum and Sweat absorbent | Required |
| Sodium silicate | Sebum and Sweat absorbent | Required |
| Calcium Silicate | Sebum and Sweat absorbent | Required |
| Magnesium alumina metasilicate | Sebum and Sweat absorbent | Required |
| Polysilicic Acid | Sebum and Sweat absorbent | Required |
| Fumed Silica | Sebum and Sweat absorbent | Required |
| Hydrated Silica | Sebum and Sweat absorbent | Required |
| Silicic Anhydride | Sebum and Sweat absorbent | Required |
| Trimethyl siloxysilicate | Film forming agent | Optional |

-continued

| Ingredient | Function | Optional/Required |
|---|---|---|
| Curcumin Analogues | Skin rejuvenating and soothing agent | Optional |
| Balloon vine extract | Skin soothing agent | Optional |
| Echium Oil | Skin soothing agent | Optional |
| Black Current Seed oil | Skin soothing agent | Optional |
| Sun flower Oil Concentrate | Skin rejuvenating oil and soothing agent | Optional |
| Tea tree oil | Skin soothing agent | Optional |
| Tulsi oil | Skin rejuvenating oil and soothing agent | Optional |

Example 5

Abrasion Resistance Study on Human Panel

Abrasion Resistance Study on Human Panel:
Resistance to Accelerated/forced Abrasion study on human panel;
Study Plan: 6 healthy male participants and 6 healthy female participants were selected. The study was a single blind crossover clinical study, in which participants were subjected to test and marketed product simultaneously one on each arm.
Gel A is the test product (composition of Example 3g) and Gel B is marketed product (Refle sport)
Procedure and Protocol:
A fixed and known amount of gel i.e. 0.1 gm was applied of the test and marketed product on a 4 cm diameter patch on the fore arm of the participants (the final concentration being 7.96 mg/cm$^2$) and allowed to air dry. Individual formulations namely Gel A (Test product) and Gel B (marketed product) were applied on any of the arm (right/left) based on pre-decided coding system. After the patch was completely dry, sponge massager was used for abrading the patch in clockwise circular motion. The process was repeated at specific intervals until the film fades away.
Observations:
Gel A and gel B both had the same transparent appearance
Upon application both gel A and gel B had the same viscous texture and were easy to apply, formed a smooth, silky, non powdery, matt like film which easily air dried in 30 mins.
Gel A was found to have higher retention on the skin as compared to Gel B when exposed to forced abrasion using a dry sponge massager. The number of cycles required to peel off the gel film was measured for each volunteer.
Mean, SEM and SD of the number of cycles required for abrasion in all the study participants (06 males and 06 females)

| Sr. No. | Gel A Cycles | Gel B Cycles |
|---|---|---|
| 1 | 75 | 35 |
| 2 | 60 | 50 |
| 3 | 50 | 35 |
| 4 | 100 | 50 |
| 5 | 60 | 35 |
| 6 | 125 | 85 |
| 7 | 100 | 75 |
| 8 | 115 | 100 |
| 9 | 135 | 70 |
| 10 | 150 | 100 |
| 11 | 130 | 100 |
| 12 | 225 | 200 |
| Mean | 110.4 | 77.9 |
| SEM (Standard Error of Mean) | 31.9 | 22.5 |
| SD (Standard Deviation) | 48.7 | 46.3 |

The results obtained from the clinical trial were subjected to two tailed 'Paired t Test' using Graph Pad Prism Software. FIG. 1 depicts the graph obtained applying Statistics using number of cycles as the variable
Tabular Results:

| Table Analyzed | Paired t test data |
|---|---|
| Column A vs Column B Paired t test | Gel A vs Gel B |
| P value | P < 0.0001 |
| P value summary | *** |
| Are means signif. different? (P < 0.05) | Yes |
| One- or two-tailed P value? | Two-tailed |
| t, df | t = 6.734 df = 11 |
| Number of pairs | 12 |

Discussions and Conclusion:
The study was based on comparison between two gels on same person hence two-tailed paired t test was applied to the data. Probability (P) of less than 0.05 is significant i.e. confidence interval is ~95% when evaluated for cycles need to peel off the film. In this case P is 0.0001 for cycles need to peel off, hence it is statistically significant. This proves that Gel A takes higher resistance time and cycles to get removed from skin.
In the present invention we have made use of an accelerated abrasion test as a surrogate measurement to estimate the residence time on the skin when used by consumers in real life situation. Thus according to the data obtained, abrasion resistance of anti-chafe product (Gel A) of example 3 g has a significantly longer residence time on skin after application when compared with the marketed product— Reflesport (Gel B).
We claim:
1. A non aqueous gel composition consisting of:
(a) one or more silicone crosspolymers selected from the group consisting of dimethicone/vinyldimethicone crosspolymers, dimethicone crosspolymers, phenylvinyldimethicone crosspolymers, dimethicone/phenylvinyl dimethicone crosspolymers, vinyl dimethicone/methicone silsesquioxane crosspolymers, dimethicone/polyethylene glycol (PEG-10/15) crosspolymers, polyethylene glycol (PEG-15)/Lauryldimethicone crosspolymers and mixtures thereof being present at 1% w/w-30% w/w of the composition;
- (b) a silicone oil being present at about 50% w/w to about 99% w/w of the composition; and
- (c) a sweat and/or sebum absorbing agent selected from the group consisting of silica silylate, magnesium alumina meta silicate, engineered particles of silica, polysilicic acids, silicic anhydride, fumed silica, hydrated silica, silica gel, silicate esters, silicate salts, starch, and combinations thereof being present at 0.1% w/w-25% w/w.

2. The non aqueous gel composition of claim 1, which is an anti-chafing gel.

3. The non aqueous gel composition of claim 1, wherein the composition when applied to the skin of a human adheres to the skin of the human with a work of adhesion of more than about 0.500 Newton·sec when measured by TA.XT plus text analyzer using a mucoadhesive rig.

4. The non aqueous gel composition of claim 1, wherein the composition when applied to the skin of a human forms a film with a coefficient of friction of less than 0.400 when measured by Automatic surface tester (method ASTM D 1894).

5. The non aqueous gel composition of claim 1, wherein the composition when applied onto the skin of a human forms an abrasion resistant film with abrasion resistance of at least 10 cycles as measured by abrasion test IS12673-1989 or ASTM D 3885.

6. The non aqueous gel composition of claim 1, wherein the composition when applied onto the skin of a human forms an abrasion resistant film with abrasion resistance of at least 12 cycles as measured by abrasion test IS12673-1989 or ASTM D 3885.

7. The non aqueous gel composition of claim 1, wherein the silicone oil is selected from the group consisting of dimethicone, cyclopentasiloxane, simethicone, methyl dimethicone, methyl trimethicone, phenyl siloxyphenyltrimethicone and trisiloxane.

8. The non aqueous gel composition of claim 1, wherein the silicone oil is about 70 to about 99% w/w of the composition.

9. The non aqueous gel composition of claim 1, wherein the sweat and/or sebum absorbing agent is starch in combination with at least silica silylate, and/or magnesium alumina meta silicate.

10. A non aqueous gel composition consisting of:
- (a) one or more silicone crosspolymers selected from the group consisting of dimethicone/vinyldimethicone crosspolymers, dimethicone crosspolymers, phenylvinyldimethicone crosspolymers, dimethicone/phenylvinyl dimethicone crosspolymers, vinyl dimethicone/methicone silsesquioxane crosspolymers, dimethicone/polyethylene glycol (PEG-10/15) crosspolymers, polyethylene glycol (PEG-15)/Lauryldimethicone crosspolymers and mixtures thereof being present at 1% w/w-30% w/w of the composition;
- (b) a silicone oil being present at about 50% w/w to about 99% w/w of the composition;
- (c) a sweat and/or sebum absorbing agent selected from the group consisting of silica silylate, magnesium alumina meta silicate, engineered particles of silica, polysilicic acids, silicic anhydride, fumed silica, hydrated silica, silica gel, silicate esters, silicate salts, starch, and combinations thereof being present at 0.1% w/w-25% w/w;
- (d) trimethylsiloxysilicate, and
  - (e) a skin rejuvenating and soothing agent selected from the group consisting of: curcumin, Balloon Vine extract, Echium Oil, Blackcurrant seed oil, sunflower oil concentrate, tea tree oil, tulsi, neem oil, coconut oil and olive oil.

\* \* \* \* \*